(12) United States Patent
Giurgiutiu et al.

(10) Patent No.: US 8,102,101 B2
(45) Date of Patent: Jan. 24, 2012

(54) PIEZOELECTRIC SENSORS

(75) Inventors: Victor Giurgiutiu, Columbia, SC (US);
James R. Kendall, New Orleans, LA (US)

(73) Assignee: University of South Carolina, Columbia, SC (US)

( * ) Notice: Subject to any disclaimer, the term of this patent is extended or adjusted under 35 U.S.C. 154(b) by 354 days.

(21) Appl. No.: 12/359,486

(22) Filed: Jan. 26, 2009

(65) Prior Publication Data

US 2009/0188319 A1 Jul. 30, 2009

Related U.S. Application Data

(60) Provisional application No. 61/062,315, filed on Jan. 25, 2008, provisional application No. 61/062,374, filed on Jan. 25, 2008.

(51) Int. Cl.
*H01L 41/08* (2006.01)

(52) U.S. Cl. ........ 310/365; 310/320; 310/321; 310/322; 310/336; 310/323.21; 73/514.34; 324/633

(58) Field of Classification Search .................. 310/365, 310/320–322, 323.21, 336
See application file for complete search history.

(56) References Cited

U.S. PATENT DOCUMENTS

| | | | | |
|---|---|---|---|---|
| 5,789,846 A | * | 8/1998 | Brown | 310/366 |
| 6,060,756 A | * | 5/2000 | Machida et al. | 257/415 |
| 6,185,814 B1 | * | 2/2001 | Okada | 29/621.1 |
| 6,281,618 B1 | * | 8/2001 | Ishitoko et al. | 310/329 |
| 6,512,364 B1 | * | 1/2003 | Okada | 73/1.08 |
| 6,925,693 B2 | * | 8/2005 | Takeuchi et al. | 29/25.35 |
| 7,213,460 B2 | * | 5/2007 | Itoh et al. | 73/649 |
| 7,579,753 B2 | * | 8/2009 | Fazzio et al. | 310/324 |
| 2009/0048789 A1 | | 2/2009 | Yu et al. | |

OTHER PUBLICATIONS

Yu, L. 2006. "In-Situ Structural Health Monitoring With Piezoelectric Wafer Active Sensor Guided-Wave Phased Arrays," *ProQuest Information and Learning Company*, pp. 1-360.

Yu, L. and Giurgiutiu, V. 2007a. "In-situ 2-D piezoelectric wafer active sensors arrays for guided wave damage detection," *Journal of Ultrasonics*, 48(2): pp. 117-134.

Yu, L. and Giurgiutiu, V. Jul. 2009 (originally published online Oct. 16, 2008). "Multi-mode Damage Detection Methods with Piezoelectric Wafer Active Sensors", vol. 20, pp. 1329-1341.

* cited by examiner

*Primary Examiner* — Jaydi San Martin
(74) *Attorney, Agent, or Firm* — Dority & Manning, P.A.

(57) ABSTRACT

A piezoelectric sensor having a plurality of electrodes deposited on a single surface of the dielectric medium is generally provided. The plurality of electrodes can define a plurality of square-shaped electrodes forming a grid on the first surface of the dielectric medium while the second electrode defines a continuous electrode. An electrode border surrounding the plurality of electrodes can be deposited on the first surface of the dielectric medium. Alternatively, the plurality of electrodes can define column-shaped electrodes, while the second electrode defines a plurality of row-shaped electrodes separated by etchings. The direction of orientation of each column-shaped electrode and the direction of orientation of each row-shaped electrode can be substantially perpendicular. A method of making a piezoelectric sensor is also provided.

10 Claims, 10 Drawing Sheets

PIEZOELECTRIC SENSORS

PRIORITY INFORMATION

The present application claims priority to two U.S. provisional patent applications: Ser. No. 61/062,315 filed on Jan. 25, 2008 entitled "Cartesian Approach to Localization of Electric Field Excitation and Harvesting within Continuous Dielectric Medium" and Ser. No. 61/062,374 filed on Jan. 25, 2008 entitled "Localized Electric Field Excitation within a Continuous Medium". Both of these provisional patent applications are incorporated by reference herein.

BACKGROUND OF INVENTION

Structural health monitoring (SHM) is an emerging field in which smart materials interrogate structural components to predict failure, expedite needed repairs, and thus increase the useful life of those components. SHM is a method of determining the health of a structure from the readings of an array of permanently-attached sensors that are embedded into the structure and monitored over time.

SHM can be performed in basically two ways, passive and active. Passive SHM consists of monitoring a number of parameters (loading stress, environment action, performance indicators, acoustic emission from cracks, etc.) and inferring the state of structural health from a structural model. In contrast, active SHM performs proactive interrogation of the structure, detects damage, and determines the state of structural health from the evaluation of damage extent and intensity. Both approaches aim at performing a diagnosis of the structural safety and health, to be followed by a prognosis of the remaining life. Passive SHM uses passive sensors which only "listen" but do not interact with the structure. Therefore, they do not provide direct measurement of the damage presence and intensity. Active SHM uses active sensors that interact with the structure and thus determine the presence or absence of damage. The methods used for active SHM resemble those of nondestructive evaluation (NDE), e.g., ultrasonics, eddy currents, etc., but they are used with embedded sensors. Hence, the active SHM can be seen as a method of embedded NDE.

In the application of this technological approach, the use of piezoelectric materials to convert electrical signals into acoustic energy (and vice versa) has found many industrial applications for sensors. One widely used active SHM method employs piezoelectric wafer active sensors (PWAS), which send and receive Lamb waves and determine the presence of cracks, delaminations, disbonds, and corrosion. Due to its similarities to NDE ultrasonics, this approach is also known as embedded ultrasonics. PWAS use a capacitor approach to create the electric field needed for excitation. PWAS have been applied to substrates and demonstrate the ability to detect and locate cracking, corrosion, and disbonding through use of pitch-catch, pulse-echo, electro/mechanical impedance, and phased array technology.

The embedded portion of the PWAS consists of physically separated piezoelectric thin plates with electrodes on their top and bottom surfaces. For array technology, the sensors must be positioned and embedded accurately relative to all other sensors in the array because geometry and location relative to one another is critical for the accuracy of the algorithms. Currently, PWAS use the substrate as a common ground. The array is created by embedding individual PWAS into a 1-D pattern, typically eight in a row with some predetermined separation, requiring each PWAS to be bonded separately in order to achieve the highest level of relative location accuracy. This approach thus is highly time consuming and often inconsistent between applicators of different competency.

Unfortunately, 1-D arrays have the limitation of being able to only see in 180 degree increments. The images received by the Embedded Ultrasonic Radar (EUSR) for 0 to 180 degrees are superimposed with the images received from the area for 180 to 360 degrees. Thus, what is left is a 180 degree field of view. However, the EUSR cannot distinguish between what occurs behind the array from what occurs in front of it.

Improvements in array technology are moving away from 1-D arrays to more complicated 2-D arrays, increasing the number of sensors by a factor of eight. For large arrays (8*8=64 sensors), the placement of the individual sensors is extremely time consuming and inaccurate. For example, U.S. patent Ser. No. 12/101,447 filed on Apr. 11, 2008, which is incorporated by reference herein, discloses that a plurality of individual sensors can be arranged in a pattern to form a 2-D phased array where each sensor is meticulously positioned and a wire is connected to each sensor.

The present invention addresses the disadvantages of current constructions and methods and provides improved methods of structural health monitoring.

SUMMARY OF INVENTION

Objects and advantages of the invention will be set forth in part in the following description, or may be obvious from the description, or may be learned through practice of the invention.

The present disclosure is generally directed toward, in one embodiment, a piezoelectric sensor. The sensor has a dielectric medium defining a first surface and an opposite surface. A plurality of electrodes is deposited on the first surface of the dielectric medium such that the electrodes are separated by etchings. A second electrode is positioned on the opposite surface of the dielectric medium.

For instance, the plurality of electrodes can define a plurality of square-shaped electrodes forming a grid on the first surface of the dielectric medium while the second electrode defines a continuous electrode. An electrode border surrounding the plurality of electrodes can be deposited on the first surface of the dielectric medium.

The plurality of electrodes can, in one particular embodiment, define column-shaped electrodes, while the second electrode defines a plurality of row-shaped electrodes separated by etchings. The direction of orientation of each column-shaped electrode and the direction of orientation of each row-shaped electrode can be substantially perpendicular.

The piezoelectric sensor can be utilized in an embedded ultrasonic structural radar.

Also, a method of making a piezoelectric sensor is generally provided. A continuous electrode is deposited on a first surface of a dielectric medium. This continuous electrode can be etched to form a plurality of electrodes on the first surface of the dielectric medium such that the electrodes are separated by etchings. A second electrode can be deposited on an opposite surface of the dielectric medium.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1:
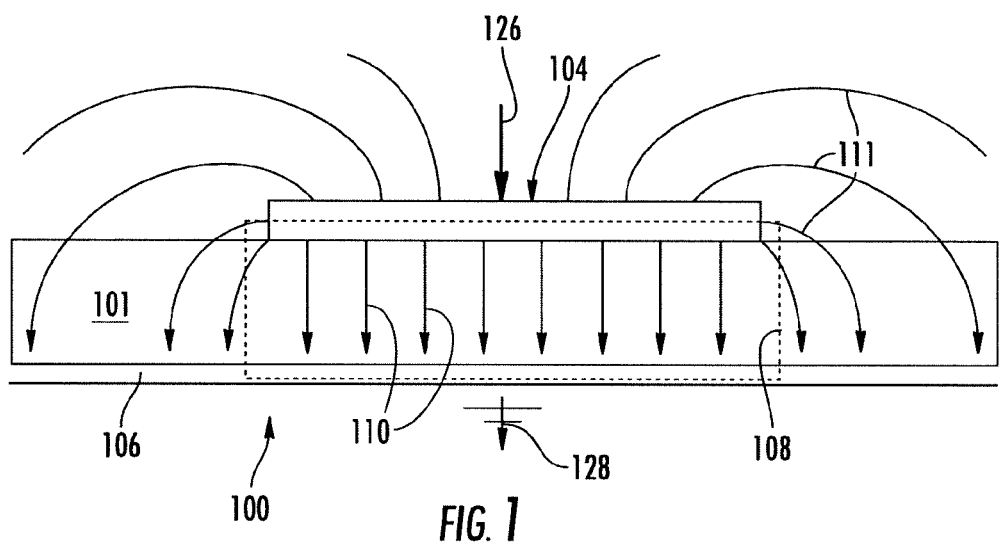
FIG. 1 shows a simplified drawing of the electric field flux profile.

Repeat use of reference characters in the present specification and drawings is intended to represent the same or analogous features or elements of the present invention.

DETAILED DESCRIPTION OF INVENTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, a single continuous layer piezoelectric material for use as a 2-D piezoelectric wafer active sensor is disclosed. Additionally, a method of independent localization of single and multiple electric fields within a continuous dielectric medium through the control of electrode geometry is generally disclosed. Through these continuous dielectric mediums, the use and tedious placement of multiple wafers can be avoided because a single wafer can be utilized to perform the structural health monitoring. The use of a single wafer saves materials, space, and effort in the production, placement, and use of the structural health monitoring through a single piezoelectric wafer active sensor.

I. 2-D PWAS Array with Sliced Electrodes

In one embodiment, the present invention is generally directed to a continuous dielectric medium having a plurality of electrodes positioned on one surface of the continuous dielectric medium. This embodiment can allow for control of the geometry, orientation, and position of an electric field within a continuous dielectric medium created by voltage difference between two electrodes. Additionally, this embodiment can allow for control of the geometry, orientation, and position of a gathered electric field within the continuous dielectric medium created by any electric charge within the dielectric medium. Thus, a continuous 2-D piezoelectric array with equivalent boundary conditions for use in sensors (e.g., a piezoelectric wafer active sensor) can be fabricated.

Consider an infinite continuous plate dielectric medium with thickness t, with a continuous electrode on one surface, and a circular electrode with a finite radius $r_s$ on the other surface. When a voltage difference is created between the two electrodes, the material that receives the highest electrical field flux will be located near the axis of symmetry between the two electrodes. As $r_s$ becomes large relative to t the percentage of the flux which flows normally between the two electrodes increases.

A simplified drawing of the electric field flux profile is given in FIG. 1. The sensor 100 has a dielectric medium 101 between an electrode 104 and an opposite, continuous electrode 106. When a signal is passed through the sensor 100 from incoming signal wire 126 to ground wire 128, the localized field 108 is formed out of the electric field flux 110. As show, most of the electric field 110 passes from the top electrode 104 through the dielectric medium 101 to the bottom electrode 106 creating the electric field flux 110. Some leakage 111 may occur outside of the electric field flux 110, without significant interference with the end use.

Without wishing to be bound by theory, it is believed that if an infinite continuous plate of dielectric medium with a continuous electrode on the grounding surface is considered, and the electrodes on the top "signal" surface are divided into m areas, m separate capacitors are effectively created because the electric fields which are created via application of a signal to any one of the signal electrodes will be localized to the volume between that signal electrode and the ground. In this manner, the electrodes are used to define the portion of the dielectric medium which will experience the electric field rather than the complete physical separation of sensors. This allows the dielectric medium to be deposited as a continuous plate with the material of each sensor controlled by the thickness of the dielectric medium and the size and shape of the signal electrode. If the thickness of the dielectric medium is very small compared to the geometry of the signal electrode (such as in the case of PWAS), the medium excited by an electric field at any location between the electrodes will be very close to a normal projection of the signal electrode onto the continuous ground electrode.

A finite square plate of a dielectric medium with continuous electrodes on both the grounding surface and the top surface is essentially a typical square PWAS. If one of the electrodes is chemically or mechanically divided into a grid pattern, then separate capacitors are effectively created using the dielectric medium, where the sum of which will be approximately equal to the original capacitor.

Figures 2A, 2B:
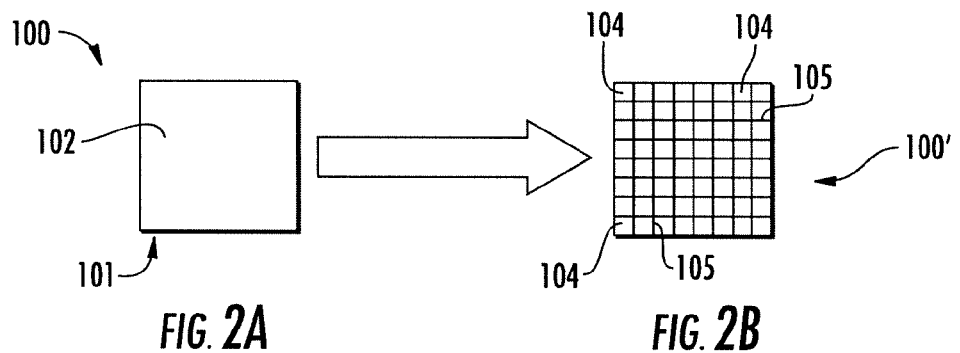
FIG. 2a shows a continuous electrode deposited on a continuous dielectric medium.
FIG. 2b shows sixty-four square-shaped electrodes divided by etchings on a continuous dielectric medium.

For example, FIG. 2a shows a continuous electrode 102 deposited on a continuous dielectric medium 101, such as in the form of a single wafer. FIG. 2b shows the continuous electrode 102 after separation of the continuous electrode by etchings 105 into sixty-four square-shaped electrodes 104 on the continuous dielectric medium 101 forming a grid pattern on the dielectric medium. Thus, the single wafer 100' now effectively defines sixty-four electrodes 104.

Of course, the number, size, and shape of electrodes formed from the continuous electrode on the dielectric layer can vary as desired. In most embodiments, the electrode can be divided into a grid pattern of substantially equal size squares, such as shown in FIG. 2b. For example, the grid of square-shaped electrodes 104 shown in FIG. 2b defines eight substantially parallel rows that are approximately equally spaced across the surface of the electrode. The rows are substantially perpendicular to and intersect eight substantially parallel columns that are approximately equally spaced across the surface of the electrode. The eight rows intersect the eight columns to define a grid of sixty-four square electrodes.

The rows and columns can be created by existing microelectronics etching methods (e.g., chemical etching, mechanical etching, etc.)

To actuate each sensor, a signal wire must be connected to each of the new smaller electrodes. Thus, for each smaller electrode to be functional in the embodiment shown in FIG. 2b, sixty-five wires must be connected (one to each of the sixty-four square-shaped electrodes 104 and one to the electrical ground). As such, 64 capacitors are available on a single piezoelectric wafer active sensor for use in a structural health monitoring system.

In one particular embodiment of the single piezoelectric wafer active sensor with a plurality of smaller electrodes positioned on one electrode surface of the dielectric medium, an electrode border can surround the plurality of smaller electrodes. The electrode border provides uniformity to the plurality of electrodes on the dielectric medium enabling more consistent results provided by each of the smaller electrodes, especially those smaller electrodes positioned on the outer areas of the dielectric medium. This electrode border is, in most embodiments, unconnected to any lead wire and is provided on the dielectric medium to enhance the accuracy of the PWAS.

Figure 9:
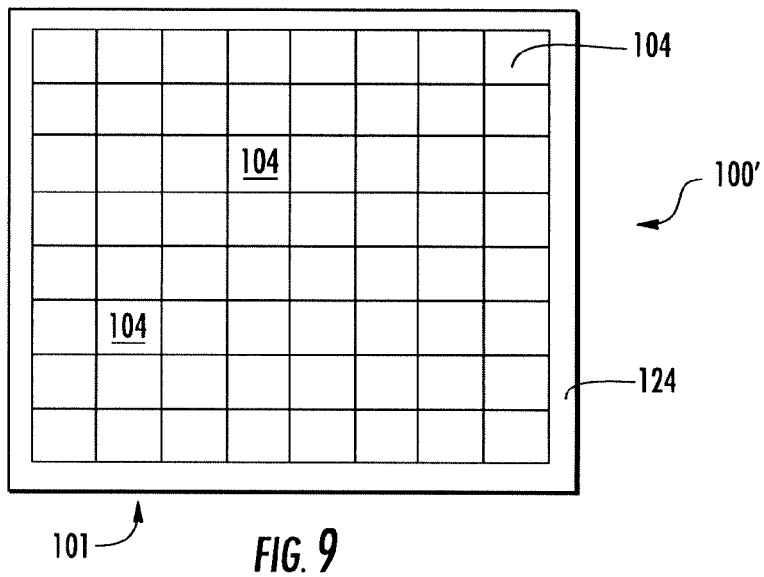
FIG. 9 shows an exemplary single piezoelectric wafer active sensor having a plurality of square-shaped electrodes surrounded by an electrode border.

FIG. 9 shows an exemplary single piezoelectric wafer active sensor 100' having a plurality of square-shaped electrodes 104 positioned on one surface of the dielectric medium 101. An electrode border 124 surrounds the grid formed by the plurality of square-shaped electrodes 104. This electrode border 124 helps to provide consistency to square-shaped electrodes 104 positioned on the parameter of the grid as described in Example 2 below.

II. Cartesian Wafer with Etched Electrodes

In one particular embodiment, the present invention is generally directed to a method of double electrode projection to reduce wiring of localized piezoelectric transducers arranged in a grid pattern according to this method.

Figures 12A, 12B:
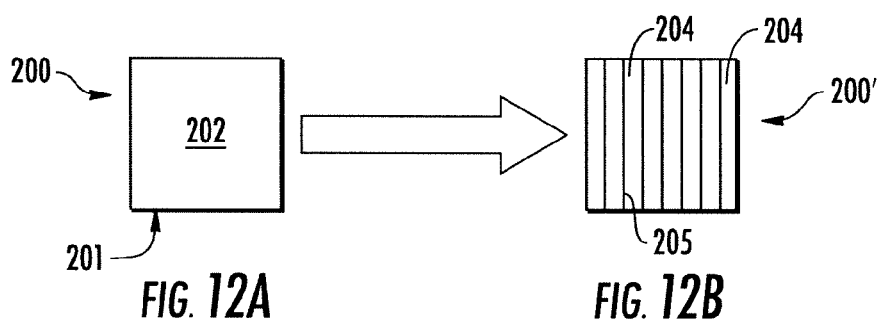
FIGS. 12a and 12b show a continuous electrode divided into 8 column-shaped electrodes.

According to this embodiment, a typical square piezoelectric wafer active sensor (PWAS) having a finite square plate of dielectric medium with continuous electrodes on both the grounding surface and the top surface is utilized. Eight separate capacitors can be created by dividing one of the electroded sides by etching (chemically or mechanically) into a column pattern. These etch lines can be substantially parallel and approximately equally spaced apart. However, the exact size and shape of the columns may vary as desired. For example, FIGS. 12a and 12b show that the continuous electrode 202 on the dielectric medium 201 of the sensor 200 has been divided into 8 column-shaped electrodes 204 (e.g., in the y-direction) separated by vertical etch lines 205. The sum of the eight column-shaped capacitors is approximately equal to the original capacitor. To actuate each active sensor, a signal wire is connected to each of the new column shaped electrodes 204.

Figures 13A, 13B:
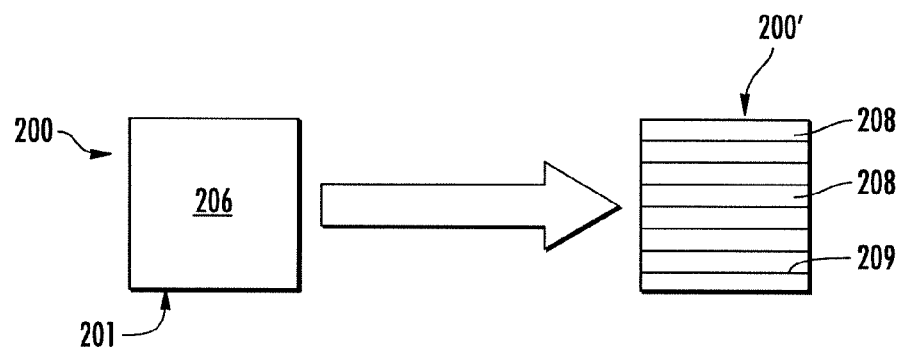
FIGS. 13a and 13b show a continuous electrode divided into 8 row-shaped electrodes.

The opposite continuous electrode 206 can also be divided (chemically or mechanically) into row-shaped electrodes 208 separated by horizontal etch lines 209. These horizontal etch lines 209 can be substantially parallel and approximately equally spaced apart. However, the exact size and shape of the rows may vary as desired. For example, FIG. 13b shows that the continuous electrode 206 of FIG. 13a has been divided into eight row-shaped electrodes 208 (e.g., in the x-direction) separated by horizontal etch lines 209. The sum of the eight capacitors is approximately equal to the original capacitor. To actuate each sensor, a signal wire is connected to each of the new smaller electrodes.

Figure 14:
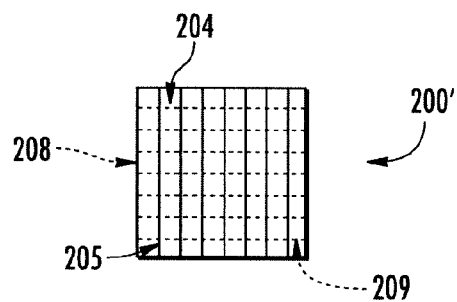
FIG. 14 shows that sixty-four separate capacitors are created if one electrode is divided into eight substantially equal column-shaped electrodes and the opposite electrode is divided into eight substantially equal row-shaped electrodes.

No matter the size or shape of the columns and rows, the column-shaped electrodes 204 and row-shaped electrodes 208 can be oriented substantially perpendicular to each other. As such, the column-shaped electrodes 204 on one side of the dielectric medium and the row-shaped electrodes 209 on the opposite side of the dielectric medium form a grid pattern through the dielectric medium. FIG. 14, for instance, shows that sixty-four separate capacitors are created if one electrode is divided into eight substantially equal column-shaped electrodes 204 (as shown in FIG. 12b) and the opposite electrode is divided into eight substantially equal row-shaped electrodes 208 (as shown in FIG. 13b) such that the columns and rows are oriented perpendicularly to each other. The sum of the sixty-four capacitors can be approximately equal to the original capacitor.

In this embodiment, a wire is connected to each row-shaped electrode 208 on one surface of the dielectric medium 201 and to each column-shaped electrode 204 on the opposite surface of the dielectric medium. For the embodiment shown in FIG. 14, this particular configuration thus requires only 16 wires to be connected (one to each column-shaped electrode 204 and one to each row-shaped electrode 208). However, as explained below, this configuration results in a piezoelectric wafer active sensor 200' effectively having 64 capacitors on a single piezoelectric wafer active sensor.

Figure 15:
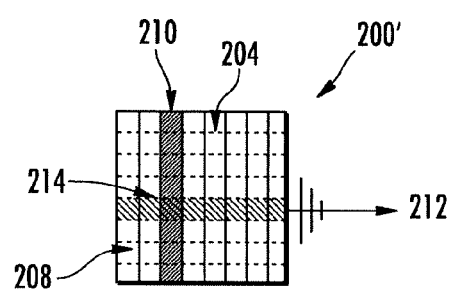
FIG. 15 shows the effective area of sensor actuation defined by the overlap of the activated column-shaped electrode and the activated row-shaped electrode.

The resulting piezoelectric wafer active sensor utilizes a Cartesian field localization approach to define a grid of capacitors. The projection of any column-shaped electrode 204 onto any row-shaped electrode 208 results in the projection occurring in one area defined by the overlap of the row-shaped electrode and the column-shaped electrode. Specifically, the effective area 214 of sensor actuation is defined by the overlap of the activated column-shaped electrode 204 and the activated row-shaped electrode 208 through the appropriate signal wire 210 and the appropriate ground wire 212, as shown in FIG. 15. Through this method, a 2-D array can be fabricated using 16 wires instead of 65.

Figure 16A:
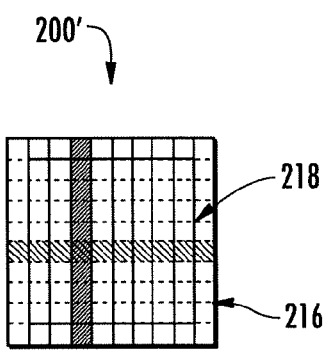
FIGS. 16a and 16b show a perimeter electrode area surrounding the edge of the grid formed by the activated column-shaped electrodes attached to incoming signal wires and row-shaped electrodes attached to ground wires.
Figure 16B:
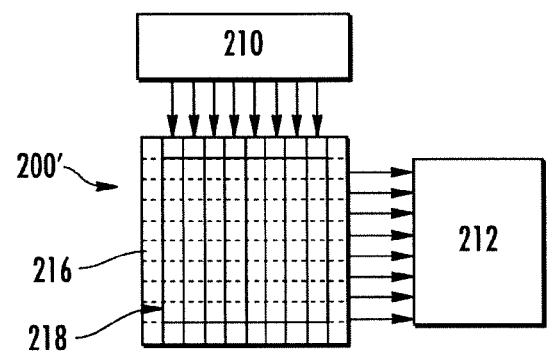

In one particular embodiment, an array can be fabricated such that the electrodes on either side of the dielectric medium extend beyond the perimeter of the effective array. Thus, the grid defines an interior area of each electrode in order to maintain common boundary conditions for each sensor, especially for those sensors defined on the outer perimeter of the grid. For the sensors adjacent to the perimeter of the effective array area, the slices in the electrodes should extend beyond that perimeter in order to facilitate creation of the most consistent field characteristics within the dielectric material as possible. For example, FIGS. 16a and 16b show a perimeter electrode area 216 surrounding the edge 218 of the grid formed by the activated column-shaped electrodes 204 attached to incoming signal wires 210 and row-shaped electrodes 212 attached to ground wires 212.

Of course, the number of column-shaped electrodes and row-shaped electrodes can vary as desired to create any grid having the desired number of capacitors.

III. Embedded Ultrasonic Structural Radar

The presently disclosed piezoelectric-wafer active sensors on a single dielectric medium can be utilized in place of a plurality of wafers to form an embedded ultrasonic structural radar (EUSR). EUSR systems are disclosed in U.S. patent Ser. No. 12/101,447 filed on Apr. 11, 2008, which is incorporated by reference herein.

EXAMPLES

The following experiments are provided to illustrate the present invention and are not intended as limiting the scope of the invention:

Example 1

The preliminary results obtained with the 2-D PWAS array with sliced electrodes for tuning curves and EUSR imaging are disclosed and described herein.

Figures 3A, 3B:
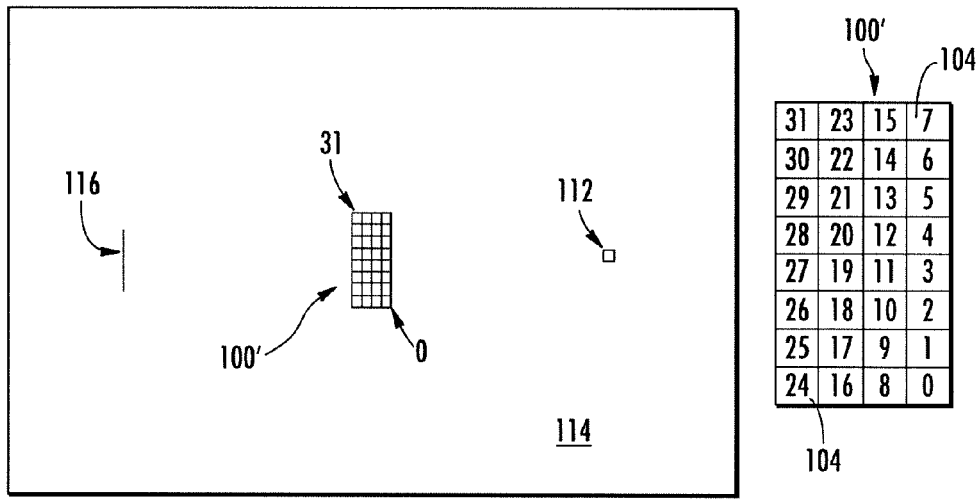
FIG. 3a shows a layout of the experimental aluminum plate defining a slice to be detected by the PWAS.
FIG. 3b shows a 2-D PWAS array sensor naming scheme

A 2-D array having 32 sensors (8 rows times 4 columns) numbered from 0 to 31 as shown in FIG. 3b) was fabricated by mechanically etching through scratching the separation lines in the surface of the electrode. This array was bonded to an aluminum plate (commercially available 2024 aluminum plate) with a T3 treatment. Previously, a slice fabricated to simulate a crack was placed in the aluminum plate. The array was used to image and locate the crack using PWAS separated only by their electrodes. An additional single PWAS with the same electrode geometry was bonded at a distance for use in creation of amplitude curves of the various Lamb wave modes as a function of frequency. A layout of the experimental plate is shown in FIG. 3a with aluminum plate 114 defining the slice 116. The sensor 100' was attached on the surface of the plate 114 along with the additional PWAS 112.

Figure 4:
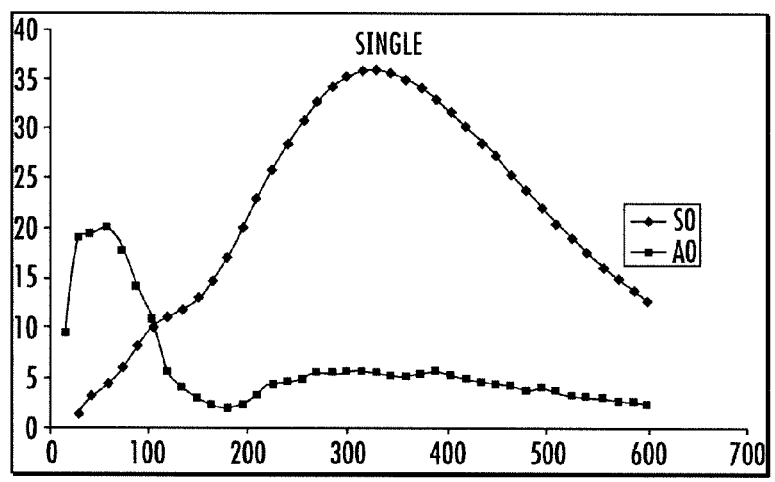
FIG. 4 shows the tuning curves between two non-bounded 5 mm PWAS.
Figure 5:
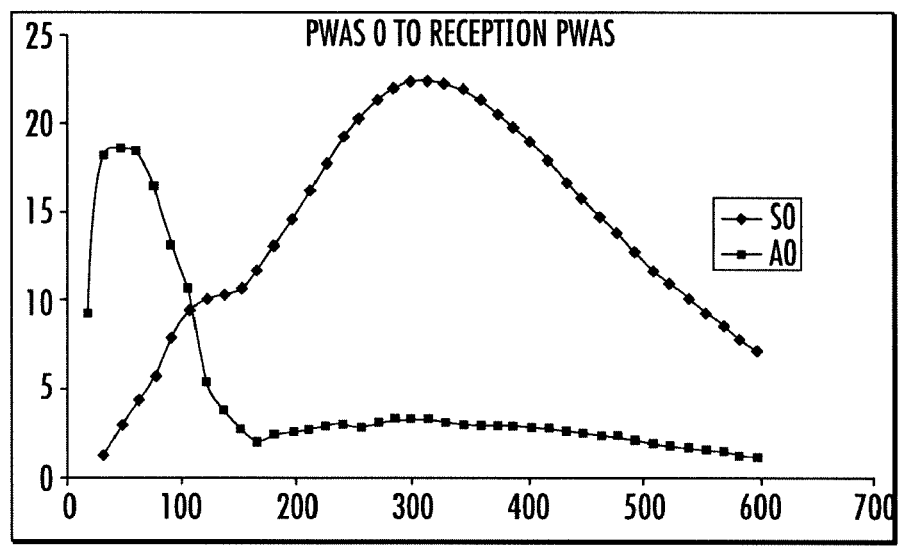
FIG. 5 shows the tuning curves of waves transmitted by PWAS 0 and received by the reception PWAS.
Figure 6:
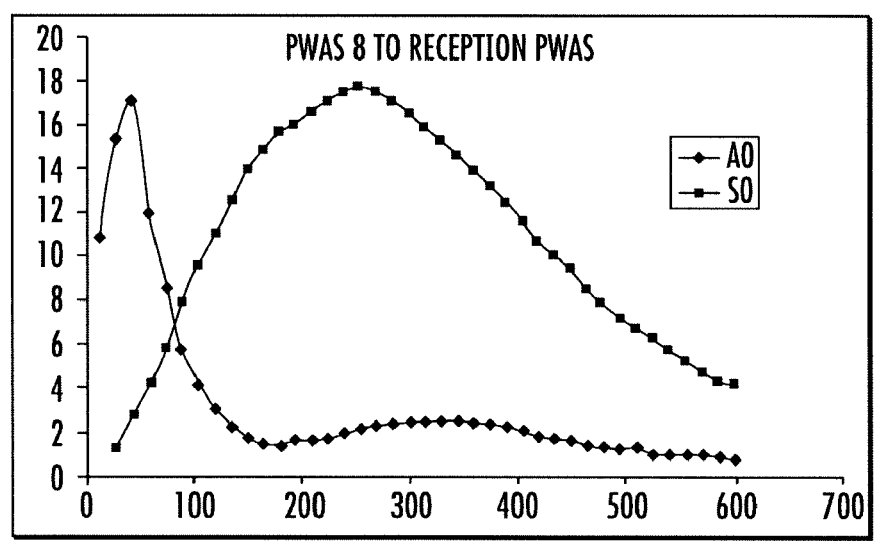
FIG. 6 shows the tuning curves of waves transmitted by PWAS 8 and received by the reception PWAS.
Figure 7:
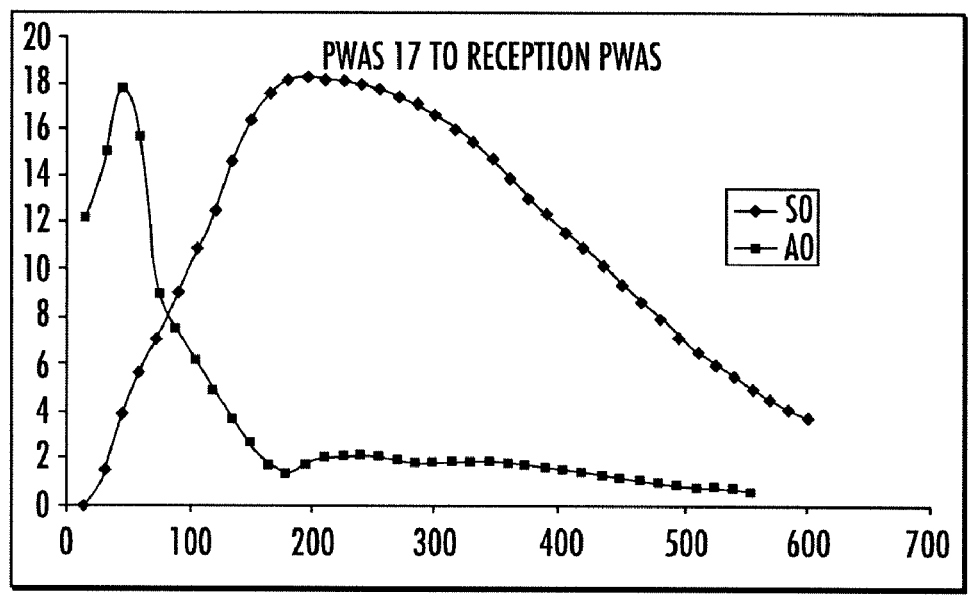
FIG. 7 shows the tuning curves of waves transmitted by PWAS 17 and received by the reception PWAS.

It was expected that the PWAS would actuate differently depending on the boundary conditions imposed by the continuous material onto each individual sensor. These conditions play a role in the amount of effective dielectric material used in each sensor, as well as the resistance to motion applied by the continuous medium. For example, the sensor PWAS number 0 of FIG. 3b has two of its sides bordered by additional sensors (i.e., sensor numbers 1 and 8) while two of its sides are the perimeter of the array. Thus, in two directions the amount of material actuated and the resistance to motion will be different than the other two directions. This has implications for the amplitudes of stress of each wave mode that is actuated at any particular frequency. The two modes which will be compared in the following data are the Lamb wave first anti-symmetric mode (A0) and the first symmetric mode (S0). At 15 kHz increments, the amplitude of both wave modes was recorded for each sensor within the 2-D array. FIG. 4 shows the tuning curves between two non-bounded 5 mm PWAS. FIG. 5 shows the tuning curves of waves transmitted by PWAS 0 and received by the reception PWAS. FIG. 6 shows the tuning curves of waves transmitted by PWAS 8 and received by the reception PWAS. FIG. 7 shows the tuning curves of waves transmitted by PWAS 17 and received by the reception PWAS. For FIGS. 4-7, the x-axis is expressed in kilohertz (kHz) and the y-axis is expressed in millivolts.

The effect of the change in the medium boundary conditions is greatest upon the S0 mode excitation (longitudinal in nature rather than shear such as the A0). The S0 tuning shape compresses lower in the frequency spectrum and is damped through the addition of material to the boundaries. The A0 mode likewise experienced some compression and damping, though the magnitudes of these changes were much smaller relative to the S0 mode.

It should be noted that signal to noise ratios rather than peak signal values is appropriate for determining the clarity of signals. In the case of PWAS 17, the piezoelectric medium was continuous in all directions. It is seen that the A0 is minimal in the range of the S0 peak for this sensor.

Figure 8:
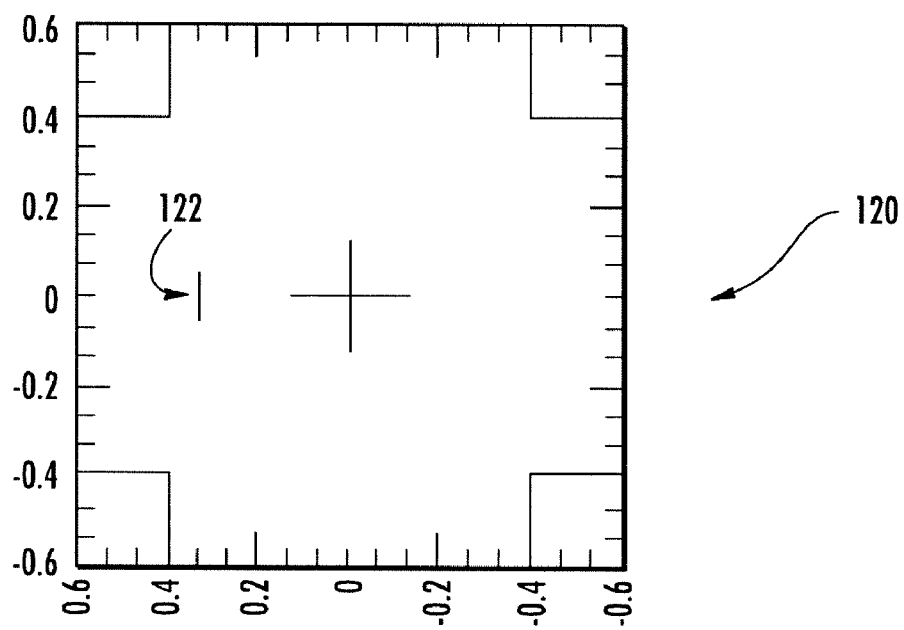
FIG. 8 shows the image of the crack as shown by EUSR from the experimental 2-D array.

Using Embedded Ultrasonic Radar, the functionality of a small 2-D array with electrode defined sensors was tested. If the PWAS are functioning properly, then the image of the scan will show the crack with correct location and geometry. The image of the crack as shown by EUSR from the 2-D array is given in FIG. 8. The image 120 shows a response 122 indicating the presence of the slice in the aluminum plate.

Example 2

Figure 10A:
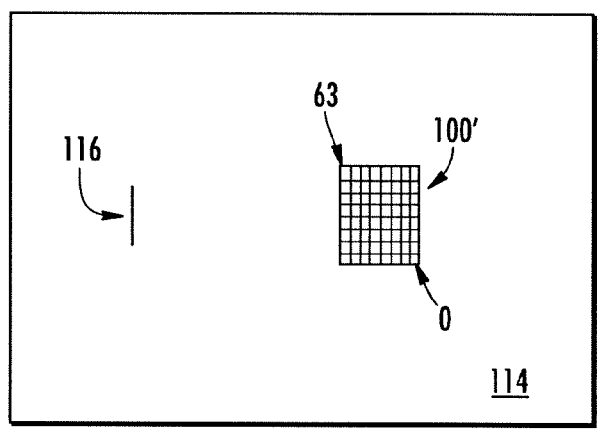
FIG. 10a shows a layout of the experimental plate from Example 2.
Figure 10B:
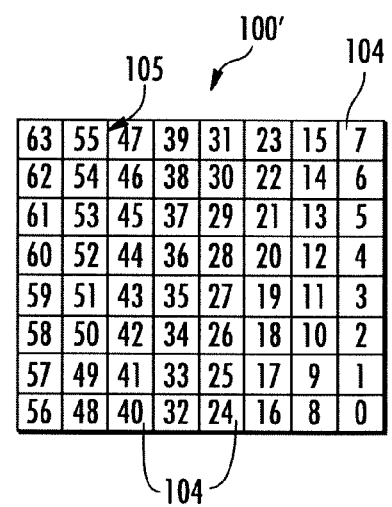
FIG. 10b shows a 2-D PWAS array sensor naming scheme.

An array designed as described in FIG. 9 was fabricated. This 2-D array 100' had 64 sensors (8 columns times 8 rows) in the form of square-shaped electrodes 104 numbered from 0 to 63 (as shown in FIG. 10b) and was fabricated using a chemical etch to separate the electrodes. This array was bonded to the same aluminum 2024 plate with T3 treatment as used in Example 1, only on the opposite side of the aluminum plate and 12 inches further from the slice 116 fabricated to simulate a crack. The array was used to image and locate the crack using PWAS separated by their electrodes. A layout of the experimental plate is given in FIG. 10a, and the naming scheme for the PWAS identification in the array is shown in FIG. 10b. The 8×8 array was investigated for feasibility in four manners as follows: capacitance, radial and thickness impedance, tuning curves, and imaging of the crack on the plate.

The measured capacitance is given in Table 1:

TABLE 1

Capacitance values for the sensors within the 2-D EP array

| | | Column | | | | | | | |
|---|---|---|---|---|---|---|---|---|---|
| | | 0 | 1 | 2 | 3 | 4 | 5 | 6 | 7 |
| Row | 0 | 6.28 | 6.12 | 5.94 | 5.97 | 6.13 | 6.01 | 6.23 | 6.45 |
| | 1 | 6.15 | 6.18 | 5.97 | 5.87 | 6.08 | 6.00 | 6.24 | 6.39 |
| | 2 | 6.17 | 6.12 | 6.03 | 5.95 | 6.09 | 5.97 | 6.23 | 6.51 |
| | 3 | 6.19 | 6.01 | 5.92 | 5.90 | 6.13 | 5.96 | 6.14 | 6.50 |
| | 4 | 6.06 | 6.06 | 6.00 | 6.17 | 6.06 | 5.95 | 6.24 | 6.46 |
| | 5 | 6.18 | 6.16 | 6.12 | 6.04 | 6.26 | 6.02 | 6.20 | 6.58 |
| | 6 | 6.47 | 6.37 | 6.30 | 6.21 | 6.29 | 6.20 | 6.30 | 6.68 |
| | 7 | 6.54 | 6.48 | 6.43 | 6.37 | 6.58 | 6.40 | 6.55 | 6.75 |

Figure 11A:
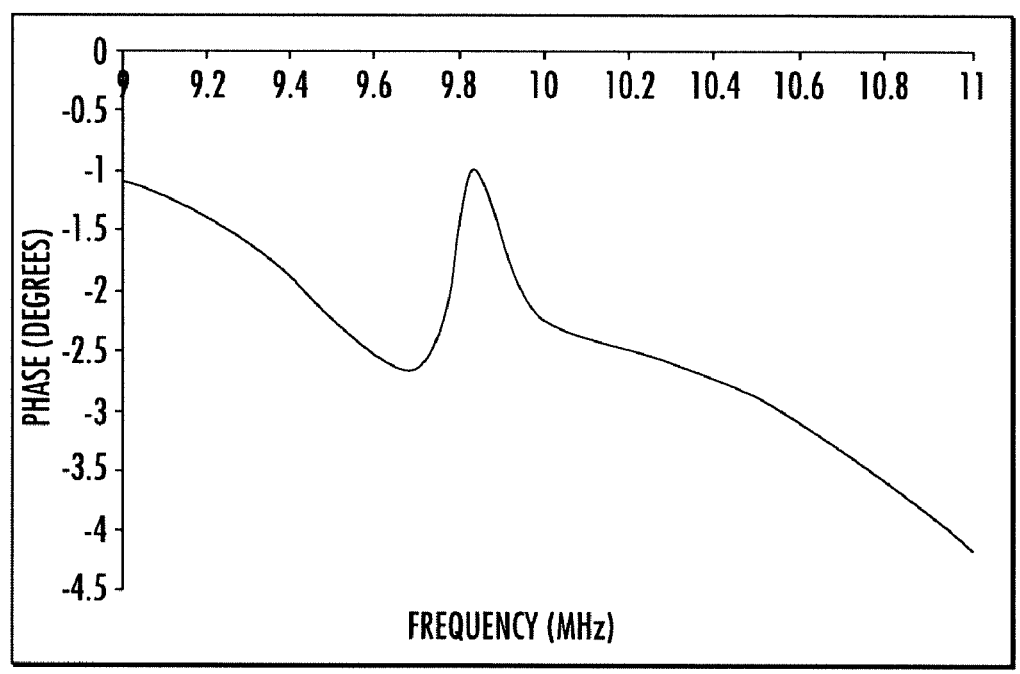
FIGS. 11a and 11b show sample impedance spectrums for Example 2.
Figure 11B:
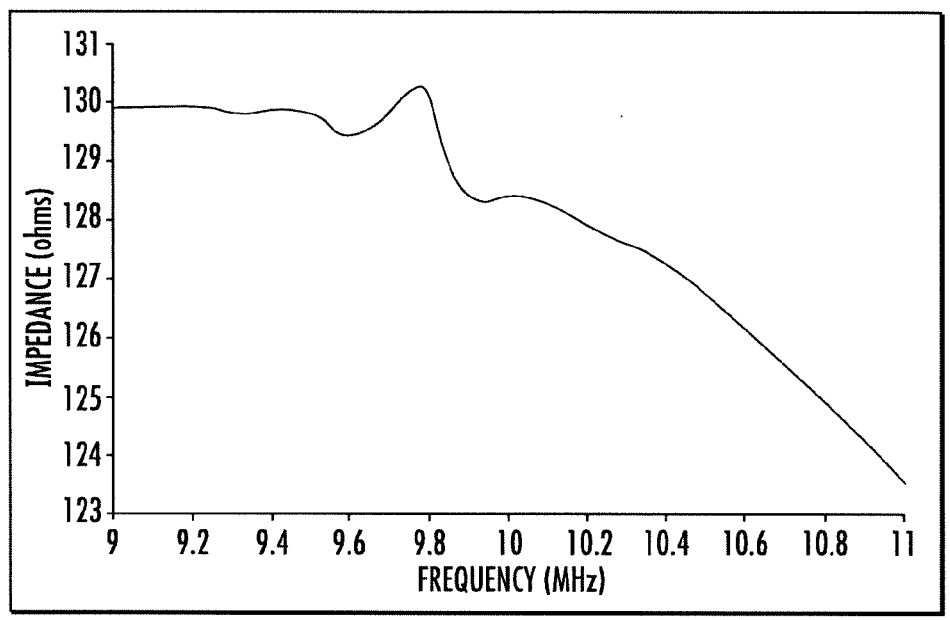

Sample impedance spectrums are given in FIGS. 11a and 11b. The radiance impedance spectrums showed no discernable peak locations as would be found in the standard PWAS. This can be explained by the lack of physical local boundaries of the piezoelectric wafer material. Since the material itself is continuous (from a local perspective) a standing wave was unlikely to occur. In contrast, the thickness direction of the material has a definite geometry associated with it (0.2 mm). These spectrums showed very good agreement with one another and indicate a clear peak in the appropriate frequency spectrum as shown in FIGS. 11a and 11b. The lack of resonance peaks due to the geometry of the piezoelectric should not affect the SHM abilities of the sensors if they are used in an impedance fashion since the resonant changes of interest for health monitoring purposes do not come from changes in PWAS geometry but rather the substrate generated resonance peaks.

Example 3

The preliminary results obtained with a prototype Cartesian wafer with etched electrodes for capacitance and resonant impedance are disclosed and described herein.

Figure 17:
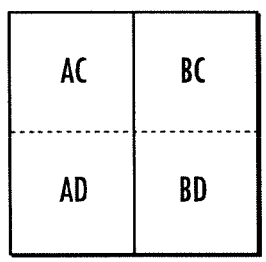
FIG. 17 shows an experimental PWAS as in Example 3 having two column-shaped electrodes on one surface and two row-shaped electrodes on the opposite surface.

A 7 mm$^2$ piezoelectric wafer was used to fabricate a prototype for this approach to excitation. The electrodes on the wafer were etched mechanically as described in FIG. 17 such that there were two "columns" on one electrode and two "rows" on the other electrode. The wafer was a construction of a 0.2 mm thickness PZT dielectric with silver sputtered electrodes on both surfaces. The objective of this kind of etching was to create a scheme to interact individually with the four quadrants of the dielectric.

The methods of interrogation to verify creation of four potential sensors (each located as the double projection of any one of the two electrodes from one surface with either of the two electrodes from the other surface) involved capacitance and impedance resonance measurements. The etched wafer was wired such that one wire was applied to each of the four rectangular electrodes. The two wires on one surface were named A and B while the wires of the opposite surface electrodes were labeled C and D. We now refer to the projection of the electrodes corresponding to wire A on to the electrode corresponding to wire C as A/C as well as the other permutations of electrode projections (A/D, B/C, B/D) following this same convention. In addition, to operate all four of the electrodes such that the wafer is expected to behave as a non-etched unit, the wires for A and B are shorted as well as the wires for C and D and this will be termed AB/CD.

The collected values for the capacitances gathered from the prototype wafer at quadrants and the whole wafer are given below in Table 2:

TABLE 2

| AB/CD | A/C | A/D | B/C | B/D |
| --- | --- | --- | --- | --- |
| 3.09 nF | 1.02 nF | 1.04 nF | 1.01 | 1.04 nF |

Figure 18:
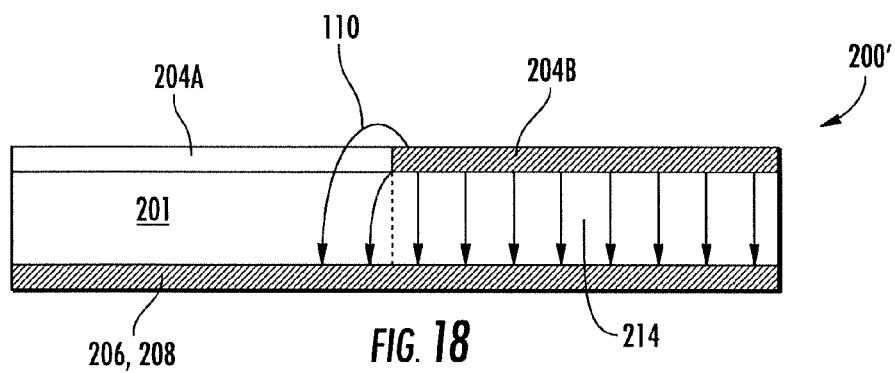
FIG. 18 shows a description of the electrical field lines indicating how the effective area of the capacitance is larger than the direct projections.
Figure 19:
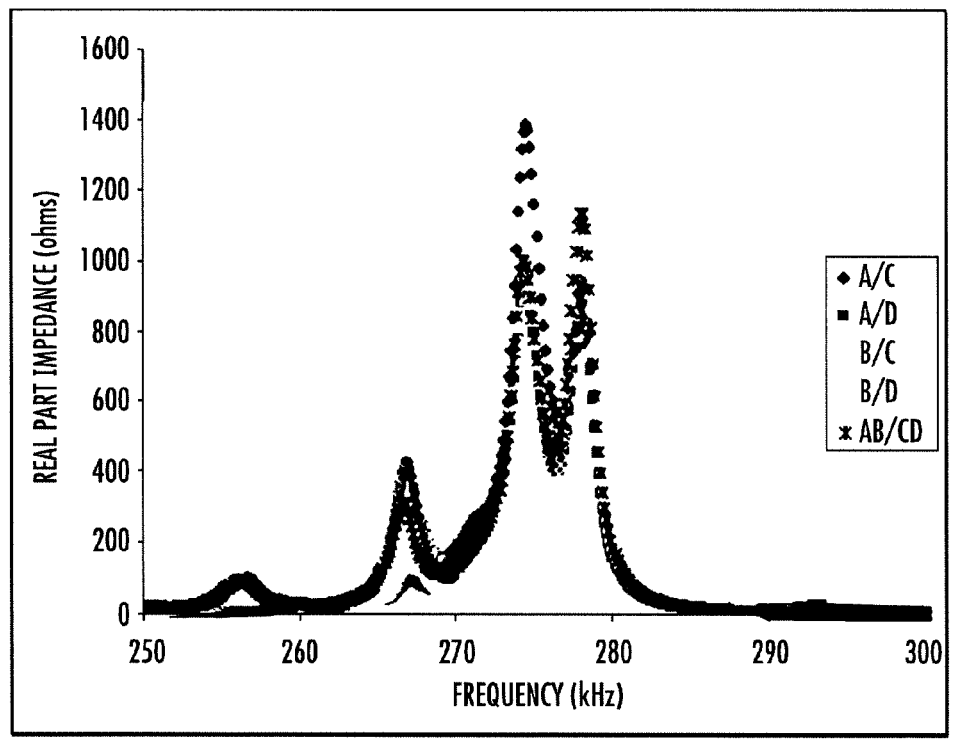
FIG. 19 shows results of Example 3.

Two observations are made based upon the gathered capacitance data. The first is that the values of the double electrode-projection quadrants are smaller than that of the full wafer. However, the second shows us that if we sum the individual capacitances from the four quadrants we receive a higher value than that of the value for AB/CD. The value suggests that the effective area of the 4 smaller sensors is approximately 33% larger than that of the area directly within the double projection. This phenomenon was expected as outlined in Examples 1 and 2. A description of the electrical field lines is given in FIG. 18 which shows how the effective area of the capacitance is larger than the direct projections. It should also be noted that this graphic only shows one aspect of the electrical field leakage outside the projection. The same phenomenon occurs on the other edge of the projection.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A piezoelectric sensor comprising:
 a dielectric medium defining a first surface and an opposite surface;
 a plurality of electrodes deposited on the first surface of the dielectric medium, wherein the electrodes are separated by etchings, wherein the plurality of electrodes define column-shaped electrodes; and
 a second electrode deposited on the opposite surface of the dielectric medium, wherein the second electrode defines a plurality of row-shaped electrodes separated by etchings.

2. The piezoelectric sensor as in claim 1, wherein the plurality of electrodes comprises a plurality of square-shaped electrodes forming a grid on the first surface of the dielectric medium.

3. The piezoelectric sensor as in claim 1, wherein a signal wire is attached to each square-shaped electrode.

4. The piezoelectric sensor as in claim 3, wherein the second electrode comprises a continuous electrode.

5. The piezoelectric sensor as in claim 4, wherein the second electrode is attached to a ground wire.

6. The piezoelectric sensor as in claim 1, wherein an electrode border is deposited on the first surface of the dielectric medium, wherein the electrode border surrounds the plurality of electrodes.

7. The piezoelectric sensor as in claim 1, wherein each column-shaped electrode is attached to an incoming signal wire and wherein each row-shaped electrode is attached a ground wire.

8. The piezoelectric sensor as in claim 1, wherein each column-shaped electrode is oriented in a first direction and each row-shaped electrode is oriented in a second direction, wherein the first direction is substantially perpendicular to the second direction.

9. The piezoelectric sensor as in claim 8, wherein an electrode border is deposited on the first surface of the dielectric medium, wherein the electrode border surrounds the plurality of column-shaped electrodes.

10. An embedded ultrasonic structural radar comprising the piezoelectric sensor as in claim 1.

* * * * *